United States Patent [19]
Clarke et al.

[11] Patent Number: 5,705,039
[45] Date of Patent: Jan. 6, 1998

[54] PROCESS FOR PURIFYING A 2,6-DIALKYLPHENOL

[75] Inventors: Sam F. Clarke, Orangeburg, S.C.; Venkataraman Ramachandran, Baton Rouge, La.; J. Steve Staton, Orangeburg, S.C.; Paul L. Wiggins, Baton Rouge, La.

[73] Assignee: Albemarle Corporation, Richmond, Va.

[21] Appl. No.: 542,612

[22] Filed: Oct. 13, 1995

[51] Int. Cl.⁶ .............. B01D 3/00; C07C 37/68
[52] U.S. Cl. .............. 203/75; 203/77; 203/80; 203/DIG. 7; 203/DIG. 9; 568/750; 568/756
[58] Field of Search .............. 203/74, 75, 77, 203/80, DIG. 19, DIG. 7; 568/756, 750

[56] References Cited

U.S. PATENT DOCUMENTS

| | | | |
|---|---|---|---|
| 4,247,721 | 1/1981 | Rugen | 568/756 |
| 5,131,984 | 7/1992 | Chan et al. | 203/6 |
| 5,175,376 | 12/1992 | Nieminen et al. | 568/781 |
| 5,262,016 | 11/1993 | Lorenzoni et al. | 203/62 |
| 5,589,598 | 12/1996 | Paiochhi | 568/756 |

*Primary Examiner*—Nina Bhat
*Attorney, Agent, or Firm*—Philip M. Pippenger

[57] ABSTRACT

Impure 2,6-diisopropylphenol (DIP) is purified by use of a distillation process in which a single distillation column is used. The process comprises: (a) subjecting the impure DIP to a first continuous distillation in the column in an inert environment to distill off lower boiling components and produce first column bottoms enriched in DIP; (b) collecting, cooling and storing the first column bottoms while continuously maintaining them in an inert environment; (c) discontinuing the first continuous distillation; (d) subjecting the first column bottoms to a second continuous distillation in an inert environment in the same column to produce a second overhead distillate composed of purified DIP. The process avoids the formation in the distilling mixtures of dose boiling impurities due to seepage of air through standard pipe flanges and fittings and consequent oxidation reactions which occur under the conditions needed for batch distillations conducted in typical industrial distillation facilities. These impurities include 2,6-diisopropylbenzoquinone, 2-isopropyl-6-isopropenylphenol, 2,6-diisopropenylphenol and 2,2-dimethyl-4-isopropyl-1,3-benzodioxole. The capital investment needed for a conventional continuous distillation facility is also avoided.

21 Claims, 4 Drawing Sheets

PROCESS FOR PURIFYING A 2,6-DIALKYLPHENOL

TECHNICAL FIELD

This invention relates to a process for converting an impure 2,6-dialkylphenol, such as produced in a catalyzed phenol ortho-alkylation process, into a highly pure product. The invention is particularly well-adapted for the purification of 2,6-diisopropylphenol produced by catalytic ortho-alkylation of phenol with propylene.

BACKGROUND

Methods for the production of ortho-dialkylated phenols such as 2,6-diisopropylphenol are well-known and reported in the literature. The most efficacious process involves reacting phenol with an olefin such as propylene using an aluminum phenoxide catalyst such as described in U.S. Pat. No. 2,831,898 to G. C. Ecke and A. I. Kolka. Modifications of this original phenol ortho-alkylation chemistry subsequently appeared, primarily involving catalyst alterations or modifications. In all such processes it is possible to achieve good selectivity in the production of the 2,6-dialkylphenol. Nevertheless the crude product mixtures typically contain impurities such as unreacted phenol, one or more monoalkylphenols, one or more dialkylphenol isomers other than the desired 2,6-dialkylphenol isomer, 2,4,6-trialkylphenol and phenolic ethers.

Recently substantial commercial requirements for highly pure 2,6-diisopropylphenol (99.8% or more) have arisen. To fulfill these requirements on an economical basis, a concomitant need has arisen for technology enabling economical large scale purification of crude phenol ortho-alkylation reaction product mixtures.

Production of high purity (99.8% and above) 2,6-diisopropylphenol by distillation is an extremely difficult operation—much more difficult than might first appear. A complicating factor is that other impurities are readily generated by oxidation reactions which occur at the elevated temperatures required during the distillation. These impurities include 2,6-diisopropylbenzoquinone, 2-isopropyl-6-isopropenylphenol, 2,6-diisopropenylphenol and 2,2-dimethyl-4-isopropyl-1,3-benzodioxole.

Laboratory studies have indicated that the formation of these impurities can be prevented if oxygen is totally excluded from the system. This, however, is not practical in most industrial distillation facilities carried out under vacuum, due to seepage of air through standard pipe flanges and fittings.

The formation of these and other impurities can be minimized by use of continuous rather than batch distillation, because the residence time—i.e., the time the material is held at the elevated temperatures—is much less in a continuous distillation. However in a situation of this kind, traditional continuous distillation requires two distillation columns to accomplish this separation whereas batch distillation requires only a single column. Because of the considerable capital investment required for distillation columns, a batch distillation would be much preferred were it not for the longer durations of exposure of the material to high temperatures and the practical difficulty of rigorously excluding air in such operations when conducted on a large scale.

U.S. Pat. No. 5,175,376 to K. M. Niemenen and P. K. Essen describes a purification procedure for 2,6-diisopropylphenol which involves subjecting the impure 2,6-diisopropylphenol to crystallization at a temperature in the range of about −25° to about 18° C. at which 2,6-diisopropylphenol crystallizes and the impurities do not, filtering and washing the 2,6-diisopropylphenol preferably with a non-polar aliphatic hydrocarbon. The solvent is removed from the product by distillation, and the product itself is recovered as a single fraction in the distillation. Such a procedure is not well suited for use in a large scale commercial operation.

U.S. Pat. No. 5,264,085 to M. Inaba, Y. Higaki, K. Jinno, M. Kataoka N. Sato and M. Honda describes a method of continuously separating components of a hydrous phenols mixture containing methanol by distillation. The method involves recovering methanol from the top of a single distillation column, dragging water containing phenols as a side stream from the recovery section of the distillation column and the dehydrated phenols as a bottom product.

SUMMARY OF THE INVENTION

This invention provides a new, economical and highly effective process for producing high purity 2,6-diisopropylphenol with the lower capital requirements of a batch distillation facility.

The process of this invention makes use of two continuous distillations in a single distillation column and at the same time makes possible the virtual elimination of the adverse in situ oxidation reactions and the production of 2,6-diisopropylphenol of purities of 99.8% and above. Thus the process provides the higher purity that normally would require two distillation columns.

In one of its embodiments, this invention provides a process for the purification of impure 2,6-diisopropylphenol which comprises: (a) subjecting the impure 2,6-diisopropylphenol to a first continuous distillation in a single distillation column in an inert environment to produce (i) a first overhead distillate of impurities boiling below the boiling point of 2,6-diisopropylphenol at the prevailing pressure and (ii) first column bottoms enriched in diisopropylphenol; (b) collecting, cooling and storing the first column bottoms while continuously maintaining them in an inert environment; (c) discontinuing the first continuous distillation; and (d) subjecting the first column bottoms to a second continuous distillation in an inert environment in the same single distillation column to produce a second overhead distillate, this being purified 2,6-diisopropylphenol.

It will be understood that the term "inert environment" as used in the specification and claims hereof means that, to the extent reasonably practicable, the material is kept free from exposure to air, oxygen or other oxidizing materials that would result in the formation of impurities in the material when subjected to elevated temperatures.

A preferred process for the purification of impure 2,6-diisopropylphenol comprises: (a) conducting a first continuous distillation by continuously feeding impure 2,6-diisopropylphenol at a first controlled rate (specified hereinafter) into an intermediate zone of a single distillation column having an inert environment therein; (b) continuously collecting a first overhead distillate of one or more impurities, and continuously collecting first column bottoms enriched in 2,6-diisopropylphenol; (c) cooling and storing the collected first column bottoms while maintaining the same in an inert environment; (d) discontinuing the feed; (e) conducting a second continuous distillation by continuously feeding the stored first column bottoms at a second controlled rate (specified hereinafter) into an intermediate zone of the same single distillation column having an inert environment therein; (f) continuously collecting purified 2,6-diisopropylphenol overhead distillate, and continuously collecting second column bottoms; and (g) cooling the collected purified 2,6-diisopropylphenol overhead distillate in an inert environment. The first controlled rate of feed is substantially equivalent to the combined rate at which the first overhead distillate and first column bottoms are being collected in the first continuous distillation, and the second controlled rate of feed is substantially equivalent to the combined rate at which the purified 2,6-diisopropylphenol overhead distillate and second column bottoms are being collected in the second continuous distillation. In a particularly preferred version of this embodiment, during the first continuous distillation first overhead distillate is refluxed from an overhead condenser and, after startup of the column and after conditions in the column have become stabilized, a portion of the condensate discharged from the overhead condenser is returned to an upper portion of the distillation column and the remainder is collected, and a portion of the first column bottoms is circulated through a reboiler and returned to the bottom of the column, and a portion of the first column bottoms is continuously collected. The portion collected can be taken as a side-stream from the flow to the reboiler or it can be taken directly from the bottom section of the column by a separate line. Similarly, during the second continuous distillation: the purified 2,6-diisopropylphenol overhead distillate is refluxed from an overhead condenser and after column startup and achievement of stable column operation, a portion of the condensate discharged from the overhead condenser is returned to an upper portion of the distillation column and the remainder is collected, and a portion of the second column bottoms is circulated through the reboiler and returned to the bottom of the column, and a portion of the second column bottoms is continuously collected. Again, the portion collected can be taken as a side-stream from the flow to the reboiler or it can be taken directly from the bottom section of the column by a separate line.

During column startup for each continuous distillation, no product as such is collected.

The above and other embodiments and features of the invention will become still further apparent from the ensuing description, appended claims, and accompanying drawings.

BRIEF DESCRIPTION OF THE DRAWINGS

In the drawings, like numerals are used in the respective Figures to represent the same elements.

FURTHER DESCRIPTION OF THE INVENTION

The process will be described in detail herein in connection with purification of impure 2,6-diisopropylphenol, for which the process is particularly well adapted. Such impure 2,6-diisopropylphenol is typically a reaction product from the catalytic ortho-alkylation of phenol with propylene, and especially wherein the catalyst used in forming the reaction product is an aluminum phenoxide catalyst in accordance with an ortho-alkylation process such as is described in the patent to Ecke and Kolka cited above. Typically such impure or crude 2,6-diisopropylphenol comprises from about 60 to about 80 wt % of 2,6-diisopropylphenol, from about 1 to about 4 wt % of phenol, from about 7 to about 21 wt % of ortho-isopropylphenol, from about 1 to about 8 wt % of 2,4,6-triisopropylphenol, and from 0 to about 4 wt % of one or more other phenolic compounds and/or phenolic ethers.

For convenience, 2,6-diisopropylphenol is hereinafter often referred to as "DIP".

Figure 1:
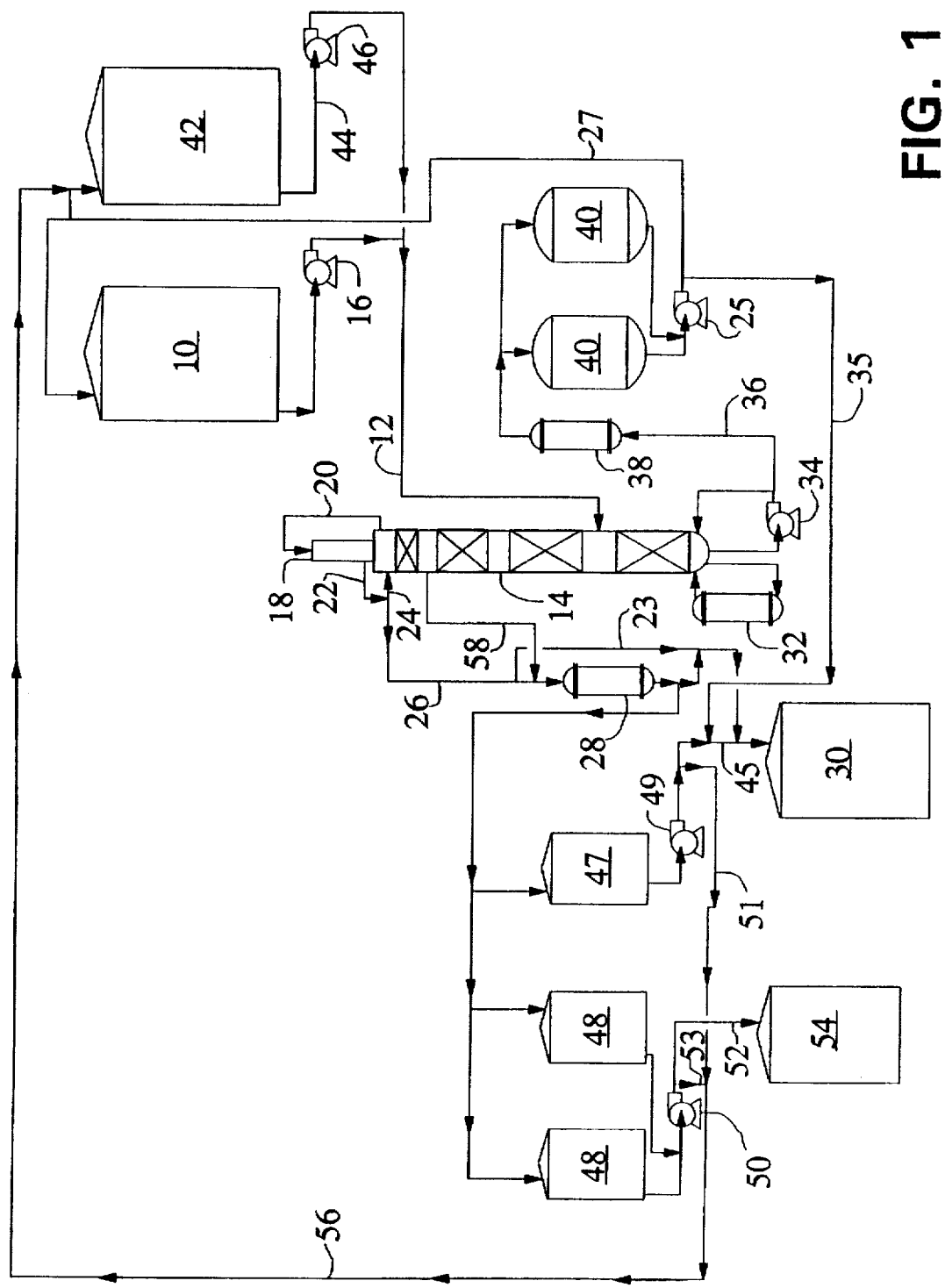
FIG. 1 is a schematic flow diagram of a preferred installation for use in conducting the process of this invention.

FIG. 1 depicts a preferred installation for conducting the purification process. It will be seen that the purification section itself comprises column 14 equipped with overhead reflux condenser 18, reboiler 32 and appropriate auxiliaries. Column 14 can be equipped with trays, but is preferably, but not necessarily, a packed column of suitable design for conducting the operations described herein.

Figure 2:
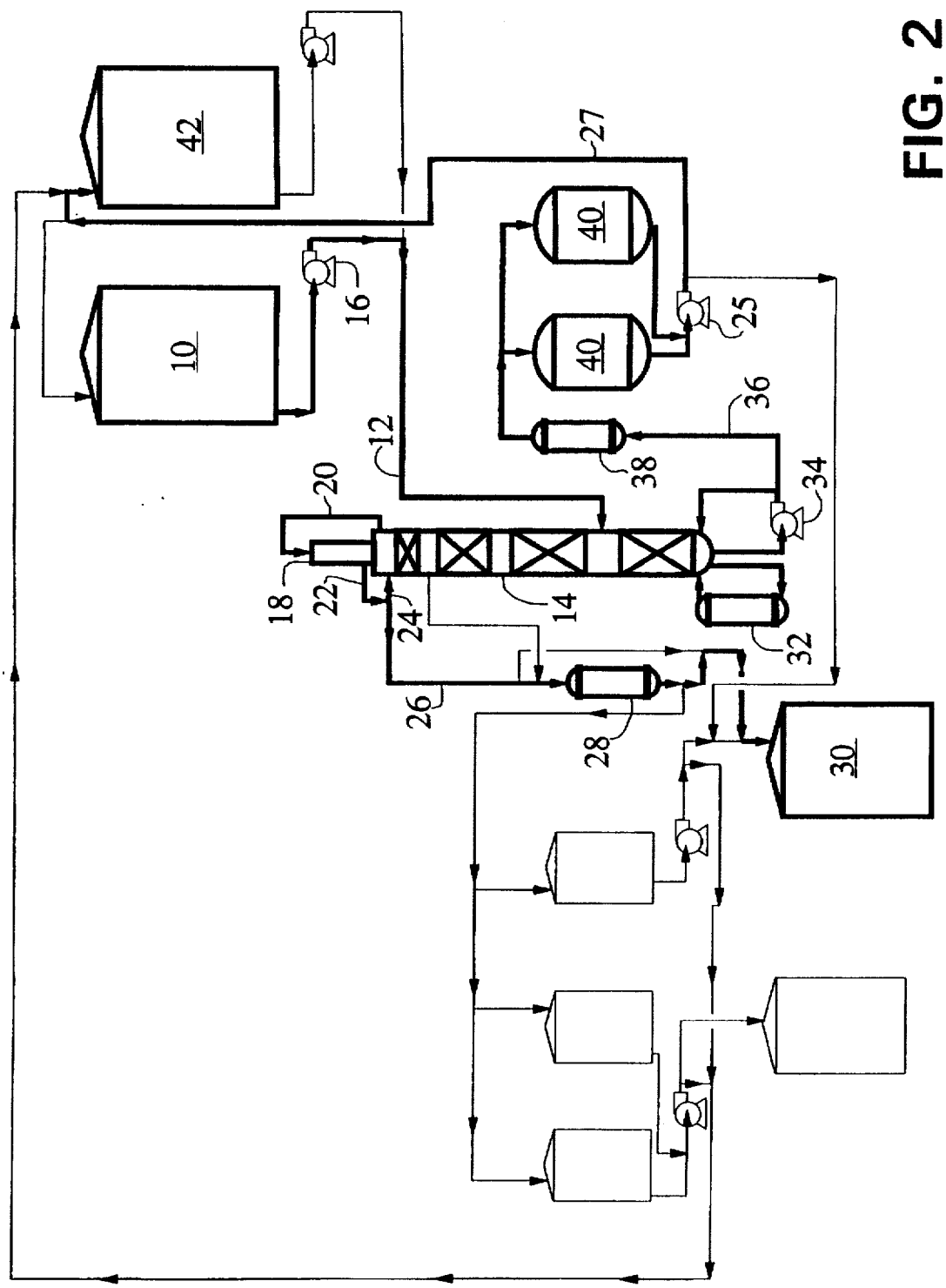
FIG. 2 is the schematic flow diagram of FIG. 1 in which the elements and flows of the system used in the first continuous distillation are highlighted by use of heavy lines.

The first continuous distillation can best be seen by referring to FIG. 2. After column startup and with column operation stabilized, crude DIP stored in tank 10 is continuously pumped via line 12 into an intermediate zone of column 14 by pump 16. In this first distillation operation, first overhead distillate from the column (light ends having lower boiling points than DIP) is transferred via line 20 into overhead condenser 18 in which it is condensed. Condensate discharged from the overhead condenser in line 22 is divided such that a portion is recirculated by line 24 back into the top portion of column 14 and the remaining portion is carried by line 26 through heat exchanger 28 in which it is cooled, and thence into tank 30 in which it is collected. The bottoms in column 14 are enriched in DIP, and a portion of these bottoms is continuously circulated through reboiler 32 to maintain column operation temperature. Another portion of the bottoms from column 14 is discharged from the column and transferred by means of pump 34 and line 36 through heat exchanger 38 for cooling and thence into one of the rundown tanks 40,40. If analysis shows that the product meets specifications for this first pass product, it is then pumped via line 27 to storage tank 42 by pump 25. To safeguard against contamination of first pass DIP product in tank 42 by first pass product that might possibly be of off-specification quality, a line (not shown) can be provided so that off-specification material from either rundown tank 40 can be pumped back to tank 10. An inert environment is maintained at all times in the entire system described.

When a suitable quantity of impure DIP has been processed in the first continuous distillation, this operation is discontinued and the operating conditions of the same distillation equipment are adjusted during startup of the second continuous distillation.

Figure 3:
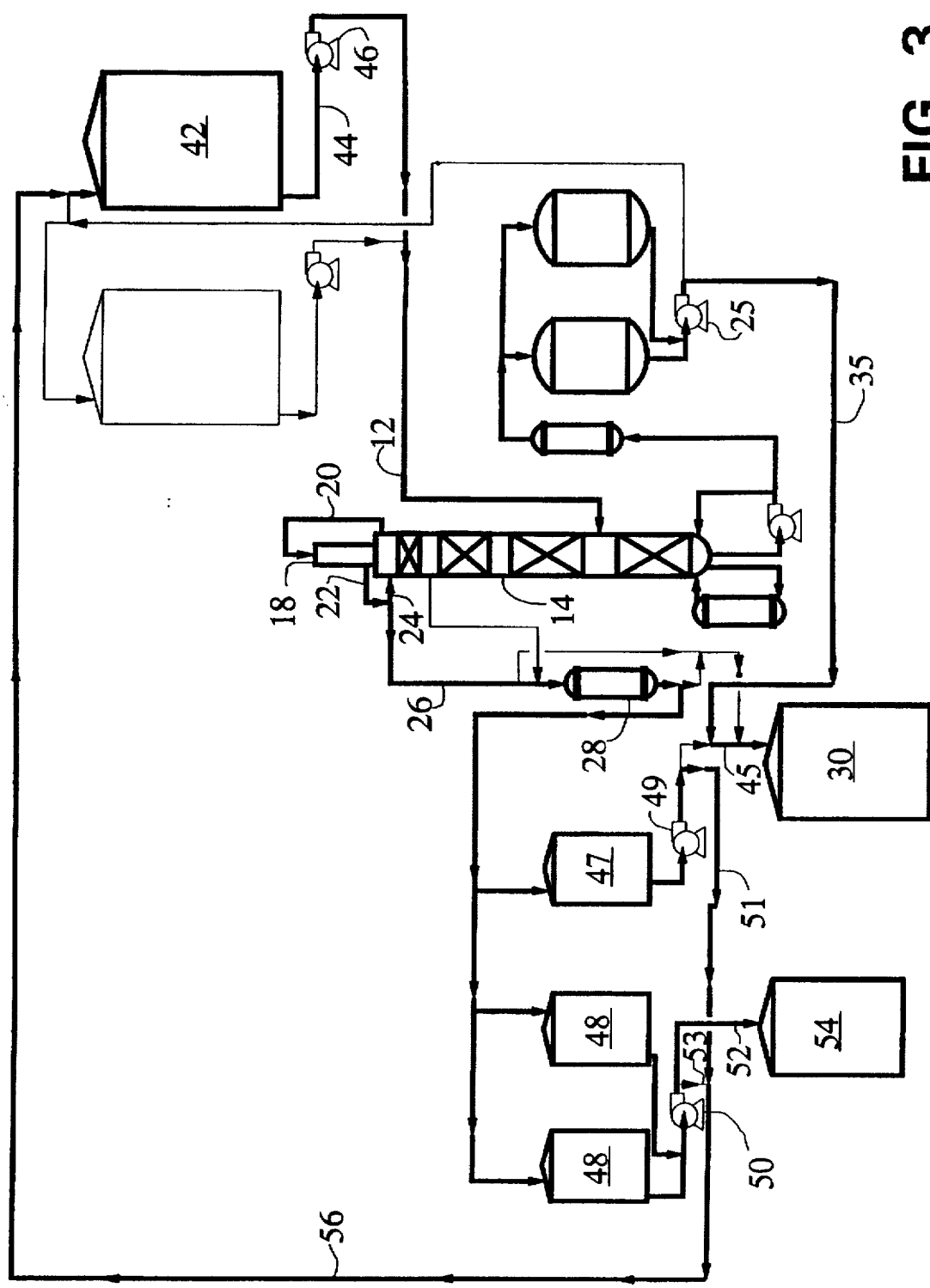
FIG. 3 is the schematic flow diagram of FIG. 1 in which the elements and flows of the system used in the second continuous distillation are highlighted by use of heavy lines.

Referring to FIG. 3, after column startup and with stabilized column operation, intermediate product enriched in DIP stored in storage tank 42 is continuously pumped via lines 44 and 12 into an intermediate zone of column 14 by pump 46. In this second distillation operation, second overhead distillate from the column (highly purified DIP) is transferred via line 20 into overhead condenser 18 in which it is condensed. Condensate discharged from the overhead condenser in line 22 is divided such that a portion is recirculated by line 24 back into the top portion of column 14 and the remaining portion is carried by line 26 through heat exchanger 28 in which it is cooled, and thence into one of product rundown tanks 48,48 for analysis. To minimize the introduction of impurities into the product rundown tanks 48,48, tank 47 is used to collect product at the start of the second distillation and at any time when the column might be upset and not producing specification product. Pump 49 is used to transfer material in tank 47 either through lines 51 and 56 back to tank 42 or through line 45 to tank 30. Product rundown tanks 48,48 are used to collect product after analyses indicate that the product meets specifications. DIP product in tanks 48,48 meeting product specifications is transferred by pump 50 and line 52 into product storage tank 54. In the event off-specification DIP product is formed, it is transferred by pump 50 and lines 53 and 56 back to tank 42 for recirculation through the distillation system. The bottoms in column 14 are handled in the same way as in the first distillation except they are transferred by pump 25 through line 35 to tank 30. An inert environment is maintained at all times in the entire system described.

Figure 4:
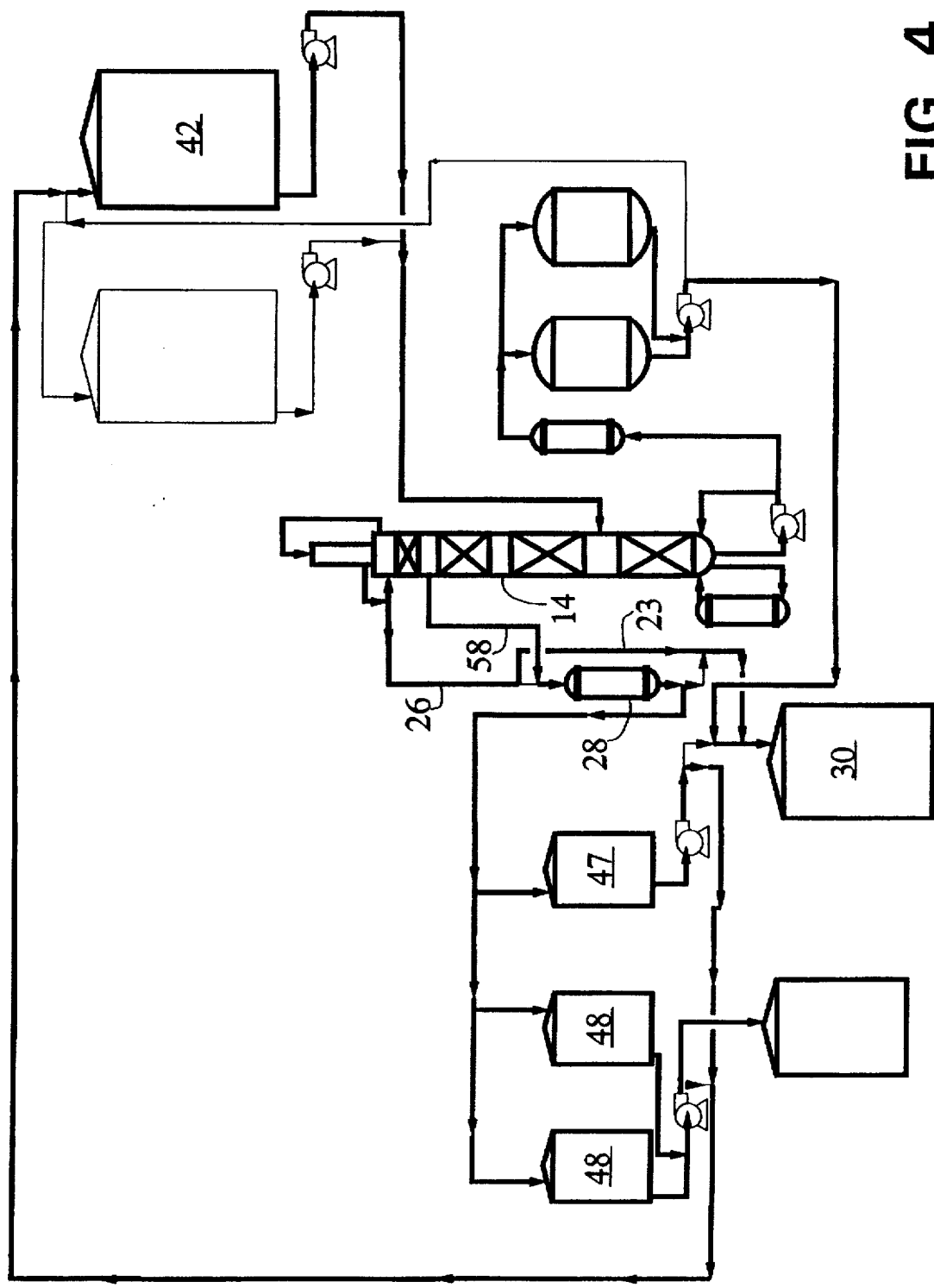
FIG. 4 is the schematic flow diagram of FIG. 1 in which the elements and flows of the system used in an optional—but for some purposes, preferred—variation of the second continuous distillation are highlighted by use of heavy lines. This distillation is referred to as the sidestream take-off distillation.

If the intermediate product stored in tank 42 after the first distillation still contains too much of the impurities boiling below the boiling point of DIP to enable the desired purity to be made in the second continuous distillation, the second distillation may be operated as depicted in FIG. 4. This sidestream take-off second distillation uses line 58 to carry the highly pure product from column 14 to heat exchanger 28 in which it is cooled, and thence into one of product rundown tanks 48,48 or to reject tank 47. The portion of the overhead condensate that is removed from the system is carried by lines 26 and 23 to tank 30. Again the environment in the system is kept inert.

To produce an even more highly purified DIP product, a third continuous distillation as is depicted in either FIG. 3 or FIG. 4 can be employed. In such case, and after adjusting the distillation operating conditions, purified product in rundown tanks 48,48 is transferred by pump 50 and lines 53 and 56 back to tank 42 for recirculation through the same distillation system as used in the second distillation or the optional sidestream take-off distillation system highlighted in FIG. 4 can be used. Whichever procedure is used, the environment in the system is again kept inert.

The operating conditions used in the continuous distillations depend to some extent upon the design of the column, the composition of the initial impure DIP to be purified, and the purity desired in the final product. In general however, for impure DIP of the type described above, and for a two-foot diameter column with fifty to sixty theoretical stages, the conditions for the first continuous distillation are as follows:

A. Temperature of first column bottoms in the bottom of the column: about 192° to about 202° C., typically about 199° C.

B. Pressure of first column bottoms in the bottom of the column: about 180 to about 235 mm Hg, typically about 220 mm Hg.

C. Temperature of overhead leaving the upper portion of the column: about 150° to about 165° C., typically about 157° C.

D. Overhead pressure in the upper portion of the column: about 165 to about 175 mm Hg, typically about 170 mm Hg.

E. Reflux temperature from the overhead condenser: about 80° to about 115° C., typically about 95° C.

F. Feed rate to column: about 13.6 kilograms (about 30 pounds) per minute maximum, typically about 7.7 kilograms (about 17 pounds) per minute, introduced above approximately the bottom third of the theoretical stages.

G. Feed rate of condensate from overhead condenser to upper portion of the column: about 4.5 to about 11.5 kilograms (about 10 to about 55 pounds) per minute, typically about 45 kilograms (about 20.4 pounds) per minute. From the above conditions, one skilled in the art can derive suitable conditions for columns of other diameters and for columns having other numbers of theoretical stages.

After subjecting impure DIP of the type described to the first continuous distillation as above, the conditions for the second continuous distillation in a two-foot diameter column with fifty to sixty theoretical stages are generally as follows:

A. Temperature of second column bottoms in the bottom of the column: about 195° to about 205° C., typically about 199° C.

B. Pressure of second column bottoms in the bottom of the column: about 130 to about 170 mm Hg, typically about 138 mm Hg.

C. Overhead pressure in the upper portion of the column: about 115 to about 125 mm Hg, typically about 120 mm Hg.

D. Reflux temperature from the overhead condenser: about 80° to about 115° C., typically about 88° C.

E. Feed rate to column: about 4.5 to about 11.5 kilograms (about 10 to about 25 pounds) per minute, typically about 8.2 kilograms (about 18 pounds) per minute, introduced above approximately the bottom third of the theoretical stages.

F. Feed rate of condensate from overhead condenser to upper portion of the column: about 6.8 to about 18.2 kilograms (about 15 to about 40 pounds) per minute, typically about 10 kilograms (about 22 pounds) per minute. Here again, one skilled in the art can derive from the above conditions and parameters, suitable conditions for columns of other diameters and for columns having other numbers of theoretical stages.

If sidestream take-off second distillation is to be used to produce higher purity DIP, distillation conditions in a two-foot diameter column with fifty to sixty theoretical stages are generally as follows:

A. Temperature of column bottoms in the bottom of the column: about 180° to about 205° C., typically about 183° C.

B. Pressure of second column bottoms in the bottom of the column: about 123 to about 160 mm Hg, typically about 130 mm Hg.

C. Overhead pressure in the upper portion of the column: about 115 to about 125 mm typically about 120 mm Hg.

D. Reflux temperature from the overhead condenser: about 50° to about 115° C., typically about 60° C.

E. Feed rate to column: about 1.8 to about 6.8 kilograms (about 4 to about 15 pounds) per minute, typically about 2.7 kilograms (about 6 pounds) per minute, introduced above approximately the bottom third of the theoretical stages.

F. Feed rate of condensate from overhead condenser to upper portion of the column: about 6.8 to about 16.3 kilograms (about 15 to about 36 pounds) per minute, typically about 10 kilograms (about 22 pounds) per minute.

G. Product flow rate from upper side portion of the column: about 1.8 to about 6.4 kilograms (about 4 to about 14 pounds) per minute, typically about 2.35 kilograms (about 5.2 pounds) per minute.

The above conditions will enable one skilled in the art to derive suitable conditions for columns of other diameters and for columns having other numbers of theoretical stages.

Several batch distillation experiments were carried out to study the effect of an air leak on impurity formation distillation temperatures. The starting material a crude DIP product formed by aluminum phenoxide catalyzed ortho-alkylation of phenol with propylene which had been subjected to a standard washing procedure to remove catalyst residues. The experiments were designed so as to allow a known quantity of air to be dialed into the system and to monitor the corresponding levels of impurities in various distillate fractions. The data indicates that them is a linear correlation between the mount of air and the impurity level. The results are presented in Tables 1 and 2 wherein percentages are GC area percentages, except as otherwise specified. A single impurity, 2-isopropenyl-6-isopropylphenol was used as the marker (i.e., as an indicator of impurity formation caused by oxidation under the distillation conditions). The conditions for the distillations when DIP was collected were as follows:

Distillation of Table 1

Temperatures: Skin=300° C.; Pot=198° C.; Overhead=194° C.

Vacuum=200 mm Hg; Reflux ratio=5:1; Total distillation time=8 hours

Air flow=36 mL/min.

Distillation of Table 2

Temperatures: Skin=3100° C.; Pot=200° C.; Overhead=193° C.

Vacuum=200 mm Hg; Reflux ratio=5:1; Total distillation time=8 hours

Air flow=16.4 mL/min.

Abbreviations used in the tables: Cum.=cumulative; OIP=ortho-isopropylphenol; 2,4=2,4-diisopropylphenol; 2,5=2,5-diisopropylphenol; TIP=2,4,6-triisopropylphenol.

The process of this invention is well suited for producing DIP in purifies of 98.5% and above, and especially for product with purifies of 99.8% or higher. In all such situations two distillation columns would normally be required for producing products of such purity on a commercial scale. While this invention has been described in detail with reference to purification of DIP, the principles described herein may be applied, with appropriate modification of the operating conditions described herein, to the purification of other impure product mixtures having similar makeup and boiling characteristics.

The entire disclosure of each and every U.S. patent referred to in any portion of this specification is incorporated herein by reference for all purposes.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for the purification of impure 2,6-diisopropylphenol which comprises:
   a) subjecting the impure 2,6-diisopropylphenol to a first continuous distillation in a single distillation column in an inert environment to produce (i) a first overhead distillate of impurities boiling below the boiling point of 2,6-diisopropylphenol at the prevailing pressure and

TABLE 1

| Cut | Wt., g | Wt. % | Cum. Wt % | OIP 18.4 | Olefin 19.0 | 20.4 | DIP 21.5 | 22.2 | 2,4 22.9 | 2,5 23.6 | TIP 24.1 |
|---|---|---|---|---|---|---|---|---|---|---|---|
| Crude | 852.8 | | | 14.94 | 0.001 | 0.027 | 69.43 | 0.157 | 0.919 | 3.04 | 7.56 |
| Trap | 5.8 | 0.7 | 0.7 | | | | | | | | |
| 1 | 44.0 | 5.2 | 5.8 | 54.948 | — | — | 0.16 | — | — | — | — |
| 2 | 155.6 | 18.2 | 24.1 | 68.695 | 0.246 | 0.013 | 28.63 | 0.010 | 0.050 | 0.010 | — |
| 3 | 77.2 | 9.1 | 33.1 | 1.238 | 0.842 | 0.022 | 96.88 | 0.060 | 0.220 | 0.050 | 0.00 |
| 4 | 83.0 | 9.7 | 42.9 | 0.091 | 0.890 | 0.017 | 98.20 | 0.067 | 0.270 | 0.059 | 0.003 |
| 5 | 88.6 | 10.4 | 53.3 | 0.021 | 0.913 | 0.015 | 98.19 | 0.083 | 0.334 | 0.076 | 0.004 |
| 6 | 90.4 | 10.6 | 63.9 | 0.020 | 0.992 | 0.016 | 97.89 | 0.107 | 0.447 | 0.110 | 0.005 |
| 7 | 32.8 | 3.8 | 67.7 | 0.055 | 2.345 | 0.022 | 95.05 | 0.153 | 0.689 | 0.307 | 0.036 |
| 8 | 87.2 | 10.2 | 77.9 | 0.014 | 1.126 | 0.034 | 96.28 | 0.240 | 1.130 | 0.543 | 0.047 |
| 9 | 30.9 | 3.6 | 81.6 | 0.032 | 0.734 | 0.063 | 94.02 | 0.435 | 2.253 | 1.644 | 0.189 |
| 10 | 6.6 | 0.8 | 82.3 | 0.428 | 0.947 | 0.077 | 92.11 | 0.525 | 2.759 | 2.100 | 0.221 |
| Pot | 111.4 | 13.1 | 95.4 | 0.039 | 0.123 | 0.043 | 12.31 | 0.329 | 2.200 | 17.660 | 53.37 |

TABLE 2

| Cut | Wt., g | Wt. % | Cum. Wt % | OIP 18.4 | Olefin 19.0 | 20.4 | DIP 21.5 | 22.2 | 2,4 22.9 | 2,5 23.6 | TIP 24.1 |
|---|---|---|---|---|---|---|---|---|---|---|---|
| Trap | 6.6 | 0.6 | 0.6 | | | | | | | | |
| 1 | 59.6 | 5.2 | 5.8 | 48.564 | — | — | 0.10 | — | — | — | — |
| 2 | 126.3 | 11.1 | 16.9 | 90.000 | 0.028 | 0.008 | 6.63 | 0.00 | 0.01 | 0.00 | — |
| 3 | 91.1 | 8.0 | 24.9 | 15.847 | 0.398 | 0.053 | 80.95 | 0.03 | 0.09 | 0.02 | — |
| 4 | 97.5 | 8.6 | 33.4 | 1.253 | 0.491 | 0.036 | 97.23 | 0.048 | 0.138 | 0.02 | 0.001 |
| 5 | 86.5 | 7.6 | 41.0 | 0.153 | 0.483 | 0.029 | 98.61 | 0.058 | 0.170 | 0.028 | 0.002 |
| 6 | 75.3 | 6.6 | 47.6 | 0.028 | 0.485 | 0.025 | 98.81 | 0.066 | 0.196 | 0.032 | 0.002 |
| 7 | 178.2 | 15.6 | 63.3 | 0.013 | 0.483 | 0.025 | 98.77 | 0.091 | 0.269 | 0.047 | 0.003 |
| 8 | 88.0 | 7.7 | 71.0 | 0.009 | 0.520 | 0.030 | 98.11 | 0.129 | 0.406 | 0.081 | 0.004 |
| 9 | 81.0 | 7.1 | 78.1 | 0.012 | 0.536 | 0.051 | 97.70 | 0.193 | 1.040 | 0.145 | 0.010 |
| 10 | 50.6 | 4.4 | 82.5 | 0.017 | 0.500 | 0.150 | 96.18 | 0.398 | 1.439 | 0.552 | 0.038 |
| 11 | 29.3 | 2.6 | 85.1 | 0.025 | 0.382 | 0.229 | 90.53 | 0.888 | 3.696 | 3.265 | 0.370 |
| Pot | 150.9 | 13.2 | 98.3 | 0.003 | 0.025 | 0.059 | 5.29 | 0.262 | 1.442 | 14.877 | 53.079 |

(ii) first column bottoms enriched in 2,6-diisopropylphenol;

b) collecting, cooling and storing the first column bottoms while continuously maintaining them in an inert environment;

c) discontinuing the first continuous distillation;

d) subjecting said first column bottoms to a second continuous distillation in an inert environment in the same single distillation column to produce a second overhead distillate composed of purified 2,6-diisopropylphenol.

2. A process according to claim 1 wherein during the first continuous distillation and after achievement of stable column conditions:

a) first overhead distillate is refluxed from an overhead condenser, a portion of the condensate discharged therefrom is returned to an upper portion of the distillation column and the remainder of said discharge is collected; and b) first column bottoms are circulated through a reboiler, a portion of the discharge therefrom is returned to a lower portion of the column, and a portion of first column bottoms is collected.

3. A process according to claim 1 wherein the impure 2,6-diisopropylphenol is a reaction product from the catalytic ortho-alkylation of phenol with propylene.

4. A process according to claim 3 wherein the catalyst used in forming said reaction product is an aluminum phenoxide catalyst.

5. A process according to claim 1 wherein prior to said first continuous distillation and during stamp of the column:

a) first overhead distillate of the column is condensed in an overhead condenser and all of the condensate discharged therefrom is returned to an upper portion of the distillation column; and b) first column bottoms are circulated through a reboiler and all of the discharge therefrom is returned to a lower portion of the column.

6. A process according to claim 5 wherein after said startup and during the first continuous distillation:

a) first overhead distillate is refluxed from an overhead condenser, a portion of the condensate discharged therefrom is returned to an upper portion of the distillation column and the remainder of the discharge is collected; and b) a portion of the first column bottoms is circulated through a reboiler and returned to a lower portion of the column, and a portion of the first column bottoms is collected.

7. A process for the purification of impure 2,6-diisopropylphenol which comprises:

a) conducting a first continuous distillation by continuously feeding impure 2,6-diisopropylphenol at a first controlled rate, into an intermediate zone of a single distillation column having an inert environment therein;

b) continuously collecting a first overhead distillate of one or more impurities, and continuously collecting first column bottoms enriched in 2,6-diisopropylphenol;

c) cooling and storing the collected first column bottoms while maintaining the same in an inert environment;

d) discontinuing said feed;

e) conducting a second continuous distillation by continuously feeding the stored first column bottoms at a second controlled rate, into an intermediate zone of the same single distillation column having an inert environment therein;

f) continuously collecting a purified 2,6-diisopropylphenol overhead distillate, and continuously collecting second column bottoms; and g) cooling the collected purified 2,6-diisopropylphenol overhead distillate in an inert environment;

said first controlled rate of feed being substantially equivalent to the combined rate at which said first overhead distillate and said first column bottoms are being collected in said first continuous distillation; and said second controlled rate of feed being substantially equivalent to the combined rate at which said purified 2,6-diisopropylphenol overhead distillate and said second column bottoms are being collected in said second continuous distillation.

8. A process according to claim 7 wherein during the first continuous distillation and after column startup:

a) first overhead distillate is refluxed from an overhead condenser, a portion of the condensate discharged therefrom is returned to an upper portion of the distillation column and the remainder of the discharge from the overhead condenser is collected; and b) a portion of the first column bottoms is circulated through a reboiler and returned to a lower portion of the column, and a portion of the first column bottoms is collected;

and wherein in the second continuous distillation and after column startup:

c) purified 2,6-diisopropylphenol overhead distillate is refluxed from an overhead condenser, a portion of the condensate discharged therefrom is returned to an upper portion of the distillation column and the remainder of the discharge from the overhead condenser is collected; and d) a portion of the second column bottoms is circulated through a reboiler and returned to a lower portion of the column, and a portion of second column bottoms is collected.

9. A process according to claim 8 wherein in the first continuous distillation the following operating conditions of the column are used for a two-foot diameter column having about 50 to about 60 theoretical stages:

A) the temperature of the first column bottoms in the bottom of the column is in the range of about 192° to about 202° C., B) the pressure of the first column bottoms in the bottom of the column is in the range of about 180 to about 235 mm Hg, C) the temperature of the overhead leaving the upper portion of the column is in the range of about 150° to about 165° C., D) the overhead pressure in the upper portion of the column is in the range of about 165 to about 175 mm Hg, and E) the reflux temperature from the overhead condenser is in the range of about 80° to about 115° C.;

wherein in the second continuous distillation:

F) the temperature of the second column bottoms in the bottom of the column is in the range of about 195° to about 205° C., G) the pressure of the first column bottoms in the bottom of the column is in the range of about 130 to about 170 mm Hg, H) the overhead pressure in the upper portion of the column is in the range of about 115 to about 125 mm Hg, and I) the reflux temperature from the overhead condenser is in the range of about 80° to about 115° C.; and wherein for a column having a different diameter and/or a different number of theoretical stages the conditions actually used are derivable from the conditions given in A) through I) hereof.

10. A process according to claim 9 wherein the first controlled rate of feed is up to about 13.6 kilograms per minute, and the second controlled rate of feed is in the range of about 4.5 to about 11.5 kilograms per minute, said feeds being introduced above approximately the bottom third of the theoretical stages of the column, and wherein for a column having a diameter other than a two-foot diameter and/or a number of theoretical stages other than about 50 to about 60, the first and second rates of feed actually used are derivable from the foregoing rates of feed.

11. A process according to claim 10 wherein in the first continuous distillation the rate at which the condensate discharged from the overhead condenser is returned to the upper portion of the distillation column is in the range of about 4.5 to about 25 kilograms per minute; wherein in the second continuous distillation the rate at which the condensate discharged from the overhead condenser is returned to the upper portion of the distillation column is in the range of about 6.8 to about 18.2 kilograms per minute; and wherein for a column having a diameter other than a two-foot diameter and/or a number of theoretical stages other than about 50 to about 60, the respective rates at which the condensate discharged from the overhead condenser is actually returned to the upper portion of the distillation column in the first and second continuous distillations are derivable from the foregoing rates of return.

12. A process according to claim 9, 10 or 11 wherein said impure 2,6-diisopropylphenol is a reaction product from the catalytic ortho-alkylation of phenol with propylene and comprises from about 60 to about 80 wt % of 2,6-diiisopropylphenol, from about 1 to about 4 wt % of phenol, from about 7 to about 21 wt % of ortho-isopropylphenol, from about 1 to about 8 wt % of 2,4,6-triisopropylphenol, and from 0 to about 4 wt % of one or more other phenolic compounds and/or phenolic ethers.

13. A process according to claim 7 wherein purified 2,6-diisopropylphenol overhead distillate from the second continuous distillation is cooled and maintained in an inert environment.

14. A process according to claim 7 wherein said second continuous distillation is a sidestream take-off distillation.

15. A process according to claim 8 wherein in the first continuous distillation the following operating conditions of the column are used for a two-foot diameter column having about 50 to about 60 theoretical stages:

A) the temperature of the first column bottoms in the bottom of the column is in the range of about 192° to about 202° C., B) the pressure of the first column bottoms in the bottom of the column is in the range of about 180 to about 235 mm Hg, C) the temperature of the overhead leaving the upper portion of the column is in the range of about 150° to about 165° C., D) the overhead pressure in the upper portion of the column is in the range of about 165 to about 175 mm Hg, and E) the reflux temperature from the overhead condenser is in the range of about 80° to about 115° C.;

wherein the second continuous distillation is a sidestream take-off distillation in which:

F) the temperature of column bottoms in the bottom of the column is in the range of about 180° to about 205° C., G) the pressure of second column bottoms in the bottom of the column is in the range of about 123 to about 160 mm Hg, H) the overhead pressure in the upper portion of the column is in the range of about 115 to about 125 mm Hg, I) the reflux temperature from the overhead condenser is in the range of about 50° to about 115° C.; and wherein for a column having a different diameter and/or a different number of theoretical stages the conditions actually used are derivable from the conditions given in A) through I) hereof.

16. A process according to claim 15 wherein the first controlled rate of feed is up to about 13.6 kilograms per minute, and the second controlled rate of feed is in the range of about 1.8 to about 6.8 kilograms per minute, said feeds being introduced above approximately the bottom third of the theoretical stages of the column, and wherein for a column having a diameter other than a two-foot diameter and/or a number of theoretical stages other than about 50 to about 60, the first and second rates of feed actually used are derivable from the foregoing rates of feed.

17. A process according to claim 16 wherein in the first continuous distillation the rate at which the condensate discharged from the overhead condenser is returned to the upper portion of the distillation column is in the range of about 4.5 to about 25 kilograms per minute; wherein in the second continuous distillation the rate at which the condensate discharged from the overhead condenser is returned to the upper portion of the distillation column is in the range of about 6.8 to about 16.3 kilograms per minute; wherein in the second continuous distillation the product flow rate from the upper side portion of the column is in the range of about 1.8 to about 6.4 kilograms per minute; and wherein for a column having a diameter other than a two-foot diameter and/or a number of theoretical stages other than about 50 to about 60:

i) the respective rates at which the condensate discharged from the overhead condenser is actually returned to the upper portion of the distillation column in the first and second continuous distillations are derivable from the foregoing rates of return; and ii) the product flow rate from the upper side portion of the column actually used in the second continuous distillation is derivable from the foregoing product flow rates.

18. A process according to claim 15, 16 or 17 wherein said impure 2,6-diisopropylphenol is a reaction product from the catalytic ortho-alkylation of phenol with propylene and comprises from about 60 to about 80 wt % of 2,6-diiisopropylphenol, from about 1 to about 4 wt % of phenol, from about 7 to about 21 wt % of ortho-isopropylphenol, from about 1 to about 8 wt % of 2,4,6-triisopropylphenol, and from 0 to about 4 wt % of one or more other phenolic compounds and/or phenolic ethers.

19. A process according to claim 7 wherein purified 2,6-diisopropylphenol overhead distillate from the second continuous distillation is subjected to at least one additional continuous distillation to further purify the 2,6-diisopropylphenol.

20. A process according to claim 19 wherein said additional continuous distillation is a sidestream take-off distillation.

21. A process according to claim 9, 10, 11, 15, 16 or 17 wherein purified 2,6diisopropylphenol overhead distillate from the second continuous distillation is subjected to at least one additional continuous distillation to further purify the 2,6-diisopropylphenol, wherein said at least one additional continuous distillation comprises 1) continuously feeding purified 2,6-diisopropylphenol overhead distillate from the second continuous distillation at a third controlled rate, specified hereinafter, into an intermediate, zone of the same single distillation column having an inert environment therein;
2) continuously collecting a more highly purified 2,6-diisopropylphenol overhead distillate, and continuously collecting third column bottoms; and
3) cooling the more highly purified 2,6-diisopropylphenol distillate in an inert environment;

said third controlled rate of feed being substantially equivalent to the combined rate at which the more highly purified 2,6-diisopropylphenol overhead distillate and the third column bottoms are being collected in said third continuous distillation.

* * * * *